US008507561B2

(12) United States Patent
Gilbert et al.

(10) Patent No.: US 8,507,561 B2
(45) Date of Patent: *Aug. 13, 2013

(54) DESENSITIZING DRUG PRODUCT

(71) Applicant: Absorption Pharmaceuticals, LLC, Newport Beach, CA (US)

(72) Inventors: Ronald Franklin Gilbert, Huntington Beach, CA (US); Anthony Cesare Capomacchia, Athens, GA (US); Jody Helfend, Calabasas, CA (US)

(73) Assignee: Absorption Pharmaceuticals, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/646,492

(22) Filed: Oct. 5, 2012

(65) Prior Publication Data

US 2013/0053447 A1 Feb. 28, 2013

Related U.S. Application Data

(63) Continuation of application No. 13/145,743, filed as application No. PCT/US2010/021705 on Jan. 22, 2010.

(60) Provisional application No. 61/146,563, filed on Jan. 22, 2009.

(51) Int. Cl.
*A61K 31/167* (2006.01)
*A61P 15/00* (2006.01)

(52) U.S. Cl.
USPC .......................................................... 514/646

(58) Field of Classification Search
USPC .......................................................... 514/626
See application file for complete search history.

(56) References Cited

U.S. PATENT DOCUMENTS

| | | | |
|---|---|---|---|
| 5,979,447 | A | 11/1999 | Al-Falahe |
| 6,299,902 | B1 | 10/2001 | Jun et al. |
| 7,414,039 | B2 | 8/2008 | Parsons |
| 7,700,076 | B2 | 4/2010 | Tamarkin et al. |
| 7,927,613 | B2 | 4/2011 | Almarsson et al. |
| 2002/0127249 | A1 | 9/2002 | Bergenstahl et al. |
| 2004/0241245 | A1 | 12/2004 | Lu et al. |
| 2005/0075407 | A1 | 4/2005 | Tamarkin et al. |
| 2005/0238733 | A1 | 10/2005 | Henry |
| 2005/0250775 | A1 | 11/2005 | Fish et al. |
| 2006/0029648 | A1 | 2/2006 | Tsaur |
| 2007/0110805 | A1 | 5/2007 | Levinson et al. |
| 2008/0206155 | A1 | 8/2008 | Tamarkin et al. |
| 2008/0206159 | A1 | 8/2008 | Tamarkin et al. |
| 2008/0234257 | A1 | 9/2008 | Gant et al. |
| 2009/0093547 | A1 | 4/2009 | Corbitt et al. |
| 2011/0002857 | A1 | 1/2011 | Tamarkin et al. |
| 2011/0015229 | A1 | 1/2011 | Zhang et al. |
| 2011/0086818 | A1 | 4/2011 | Bean et al. |
| 2011/0244043 | A1 | 10/2011 | Xu et al. |
| 2011/0263715 | A1 | 10/2011 | Pongpeerapat et al. |
| 2012/0196830 | A1 | 8/2012 | Parsons |
| 2012/0248142 | A1 | 10/2012 | Davis |

FOREIGN PATENT DOCUMENTS

| | | |
|---|---|---|
| CN | 101664555 A | 3/2010 |
| CN | 102204899 A | 10/2011 |
| KR | 2002063064 A | 8/2002 |
| KR | 10-0416646 B | 2/2004 |
| RU | 2105543 C1 | 2/1998 |
| TW | 201116274 A | 5/2011 |
| WO | WO 89/10750 A1 | 11/1989 |
| WO | WO9530408 A1 | 11/1995 |
| WO | WO 99/22717 A1 | 5/1999 |
| WO | WO 0040234 A1 | 7/2000 |
| WO | WO 0147446 A1 | 7/2001 |
| WO | WO2004078161 A1 | 9/2004 |
| WO | WO2004078163 A2 | 9/2004 |
| WO | WO 2004084878 A1 | 10/2004 |
| WO | WO 2005018530 A2 | 3/2005 |
| WO | WO 2005072751 | 8/2005 |
| WO | WO 2006022683 A1 | 3/2006 |
| WO | WO 2006121979 A3 | 12/2006 |
| WO | WO 2007073397 A1 | 6/2007 |
| WO | WO 2009007785 A2 | 1/2009 |
| WO | WO 2008152444 A3 | 6/2009 |
| WO | WO 2009114139 A2 | 9/2009 |
| WO | WO2010066203 A1 | 6/2010 |
| WO | WO 2010/080831 A1 | 7/2010 |
| WO | WO2010/085589 | 7/2010 |
| WO | WO 2011071996 A1 | 6/2011 |
| WO | WO2011074015 A2 | 6/2011 |
| WO | WO 2011/133177 A1 | 10/2011 |
| WO | WO 2011058351 A3 | 12/2011 |
| WO | WO 2012088431 A1 | 6/2012 |
| WO | WO 2012088469 A1 | 6/2012 |

OTHER PUBLICATIONS

Andersson, Karl-Erik et al., "Pharmacokinetic and pharmacodynamic features of dapoxetine, a novel drug for 'on-demand' treatment of premature ejaculation" Sexual Medicine, BJU International, 97, pp. 311-315, 2006.

AstraZeneca, "EMLA Product Information" 44, pp. 1(9)-9(9), 2006.

Athanasious, Zahariou et al., "The efficacy of duloxetine in the treatment of premature ejaculation" International Urology and Nephrology, 39, pp. 115-118, 2007.

Atikeler, M.K. et al. "Optimum usage of prilocaine-lidocaine cream in premature ejaculation" Andrologia 34, pp. 356-359, 2002.

(Continued)

*Primary Examiner* — San-Ming Hui
*Assistant Examiner* — Kathrien Cruz
(74) *Attorney, Agent, or Firm* — Knobbe, Martens, Olson & Bear, LLP

(57) ABSTRACT

Desensitizing drug products, methods of making desensitizing drug products, and methods of using desensitizing drug products including delivery of desensitizing drug products. In one embodiment, the desensitizing drug products are male genital desensitizers that comprise one or anesthetic agents and one or more melting point depressing agents.

7 Claims, 1 Drawing Sheet

(56) References Cited

OTHER PUBLICATIONS

Aydin, O.N. et al., "Antimicrobial activity of ropivacaine and other local anaesthetics" European Journal of Anesthesiology, vol. 18, No. 10, pp. 687-694, 2001.

Becker, Daniel E. et al., "Essentials of Local Anesthetic Pharmacology" Anesth. Prog. 53, pp. 98-109, 2006.

Beretta, G. et al., "Effect of an alpha-blocking agent (phenoxybenzamine) in the management of premature ejaculation" Acta Europaea Fertilitatis, European Journal of Fertility and Sterility, vol. 17, No. 1, pp. 43-45, 1986.

Berg, Jais O. et al., "Antibacterial properties of EMLA and lidocaine in wound tissue biopsies for culturing" Wound Rep Reg, 14, pp. 581-585, 2006.

Berkovitch, Matutiahu et al., "Efficacy of Prilocaine-Lidocaine in the Treatment of Premature Ejaculation" The Journal of Urology, vol. 154, No. 4, pp. 1360-1361, 1995.

Bouwsma, O.J. et al., "Characterization of Pharmacologically Important Prototropic Species Derived from a Pyridinemethanol Antimalarial by Electronic Absorption and Fluorescence Spectroscopy" Journal of Pharmaceutical Sciences, vol. 67, No. 9, pp. 1224-1228, Sep. 1978.

Broucke, Hilde Vanden et al., "Ejaculation Latency Times and Their Relationship to Penile Sensitivity in Men with Normal Sexual Function" The Journal of Urology, vol. 177, pp. 237-240, 2007.

Busato W. et al., "Topical anaesthetic use for treating premature ejaculation: a double-blind, randomized, placebo-controlled study" Bju International, vol. 93, No. 7, pp. 1464-4096 2004.

Carson, Culley et al., "Improved ejaculatory latency, control and sexual satisfaction when PSD502 is applied topically in men with premature ejaculation: results of a phase III, double-blind, placebo-controlled study" Journal of Sexual Medicine, 7:3, pp. 3179-3189, 2010.

Choi, Hyung Ki et al., "Clinical Study of SS-Cream in Patients with Lifelong Premature Ejaculation" Adult Urology 55 (2), pp. 257-261, 2000.

Choi, H.K. et al., "Safety and efficacy study with various doses of SS-cream in patients with premature ejaculation in a double-blind, randomized, placebo controlled study" International Journal of Impotence Research, 11, pp. 261-264, 1999.

Chue, Pierre, "Suspected Propranolol-Induced Delirium" The Canadian Journal of Psychiatry, vol. 49, No. 9, pp. 630-645, 2004.

DeAmicis, Lyn A. et al., "Clinical Follow-up of Couples Treated for Sexual Dysfunction" Archives of Sexual Behavior an Interdisciplinary Research Journal, vol. 14, No. 6, pp. 467-489, 1985.

Dinsmore, Wallace W. et al., "Topical eutectic mixture for premature ejaculation (TEMPE): a novel aerosol-delivery form of lidocaine-prilocaine for treating premature ejaculation" Journal Compilation Sexual Medicine, BJU International, vol. 99, pp. 369-375, 2006.

Dunn, Kate M. et al., "Sexual problems: a study of the prevalence and need for health care in the general population" Family Practice, vol. 15, No. 6, pp. 519-524, 1998.

Fisher, Alexander A., "Contact Dermatitis" Lea & Febiger Second Edition, ISBN: 0-8121-0411-0, pp. 42 and 312-313, 1973.

Food and Drug Administration, "Male genital desensitizing drug products for over-the-counter human use; proposed rule" Federal Register, vol. 50, No. 191, pp. 195-200, 1985.

Frank, Ellen et al., "Frequency of Sexual Dysfunction in "Normal" Couples" The New England Journal of Medicine, vol. 299, No. 2, pp. 111-115, 1978.

Frega, A. et al., "Vulvar and penile HPV lesions: laser surgery and topic anaesthesia" Clinical and Experimental Obstetrics & Gynecology, vol. XX, No. 1, pp. 76-81, 1993.

Girgis, S. M. et al., "A Double-Blind Trial of Clomipramine in Premature Ejaculation" Andrologia vol. 14, No. 4, pp. 364-368, 1982.

Henry, Richard et al., "TEMPE:Topical Eutectic-Like Mixture for Premature Ejaculation" Expert Opinion Drug delivery, 5(2), pp. 251-261, 2008.

Henry, R. et al. "Topical Lidocaine-prilocaine spray for the treatment of premature ejaculation: a proof of concept study" International Journal of Impotence Research, vol. 15, pp. 277-281, 2003.

International Search Report for PCT/US2010/021705 dated Dec. 14, 2010 in 4 pages.

JNJ Press Release, "ALZA Corporation Receives Letter from FDA on Dapoxetine Application" downloaded from website http://web.archive.org/web/20051107010452/http://www.jnj.com/news/20051107010452 on May 24, 2012.

Kang, L. et al., "HPLC Assay of Lidocaine in Plasma with Solid Phase Extraction and UV Detection" Journal of Pharmaceutical and Biomedical Analysis, vol. 19, pp. 737-745, 1999.

Kang, Lisheng, "Physicochemical and Formulation Studies of Two-Phase Melt Systems of Lidocaine and Ibuprofen for Enhanced Membrane Transport" Bell & Howell Information and Learning, UMI, pp. 1-143, 2000.

Kang, Lisheng et al., "Formulation and Efficacy Studies of New Topical Anesthetic Creams" Drug Development and Industrial Pharmacy, vol. 29, No. 5, pp. 505-512, 2003.

Kang, Lisheng et al., "Preparation and characterization of two-phase melt systems of lidocaine" International Journal of Pharmaceutics 222, pp. 35-44, 2001.

Kara, Hayrettin et al., "The efficacy of fluoxetine in the treatment of premature ejaculation: a double-blind placebo controlled study" The Journal of Urology, vol. 156, No. 5, pp. 1631-1632, 1996.

Kerenyi, M. et al., Lidocaine/prilocaine cream (EMLA) has an antibacterial effect in vitro, Journal of Hospital Infection, vol. 56-58, pp. 75-76, 2004.

Laumann, EO. et al., "Sexual problems among women and men aged 40-80y: prevalence and correlates identified in the Global Study of Sexual Attitudes and Behaviors" International Journal of Impotence Research, vol. 17, pp. 39-57, 2005.

Martin, Alfred, "Physical chemical principles in the pharmaceutical sciences" Physical Pharmacy Fourth Edition, Lea & Febiger, Chapter 7 and 19, pp. 145, 346, 540-541, 1993.

McCoombe, Scott G. et al., "Potential HIV-1 target cells in the human penis" Aids vol. 20, pp. 1491-1495, 2006.

McMahon CG., "Treatment of Premature Ejaculation with Sertraline Hydrochloride" International Journal of Impotence Research, vol. 10, pp. 181-184, 1998.

Morales, Alvaro et al., "A review of the current status of tropical treatments for premature ejaculation" Journal Compilation Mini Review, vol. 100, pp. 493-501, 2002.

Patrick, Donald et al., "Premature Ejaculation: An Observational Study of Men and Their Partners" J. Sex Med, vol. 2, pp. 358-367, 2005.

Reading, Anthony E. et al., "An Analysis of Self-Reported Sexual Behavior in a Sample of Normal Males" Archives of Sexual Behavior, vol. 13, No. 1, pp. 69-83, 1984.

Rowland, David L. et al., "Penile sensitivity in men with premature ejaculation and erectile dysfunction" Journal of Sex and Marital Therapy, vol. 19, No. 3, pp. 189-197, 1993.

Rowland, David L. et al., "Self-reported premature ejaculation and aspects of sexual dysfunction and satisfaction" Journal of Sex and Marital Therapy, vol. 1, pp. 225-232, 2004.

Rylander, E. et al., "Local anesthesia of the genital mucosa with a lidocaine/prilocaine cream (EMLA) for laser treatment of condylomata acuminate: a placebo-controlled study" Obstetrics and Gynecology, vol. 75, No. 2, pp. 302-306, 1990.

Schulman, Stephen et al., "Fluorescence of 6-Methoxyquinoline, Quinine, and Quinidine in Aqueous Media" Journal of Pharmaceutical Sciences, vol. 63, No. 6, pp. 876-880, 1974.

Siddiqui, Ovais et al., "The effect of iontophoresis and vehicle pH on the in-vitro permeation of lignocaine through human stratum corneum" J. Pharm. Pharmacol. vol. 37, pp. 732-735, 1985.

Singh, Parminder et al., "Dermal and Underlying Tissue Pharmacokinetics of Lidocaine after Topical Application" Journal of Pharmaceutical Sciences, vol. 83, No. 6, pp. 774-782, 1994.

Smith, Tom W., Adult Sexual Behavior in 1989: Number of Partners, Frequency of Intercourse and Risk of AIDS, Family Planning Perspectives, vol. 23, No. 3, pp. 102-107, 1991.

Symonds, T. et al., "How Does Premature Ejaculation Impact a Man's Life" Journal of Sex & Marital Therapy, vol. 29, pp. 361-370, 2003.

Szabo, Robert et al., "How does male circumcision protect again HIV infection?" BMJ, vol. 320, pp. 1592-1594, 2000.

Vignoli, G.C. Premature Ejaculation: New Electrophysiologic Approach Urology, vol. XI, No. 1, pp. 81-82, 1978.

Waldinger, Marcel D. et al., "On-Demand Treatment of Premature Ejaculation with Clomipramine and Paroxetine: A Randomized, Double-Blind Fixed-Dose Study with Stopwatch Assessment" European Urology, vol. 46, Issue 4, pp. 510-516, 2004.

Waldinger, Marcel D. et al., "A Multinational Population Survey of Intravaginal Ejaculation Latency Time" J. Sex Med., vol. 2, pp. 492-497, 2005.

Wyllie, "Clinical Trials for Aspiring Dummies (and Urologists)" BJU International, vol. 99, pp. 939-940, 2007.

Xin, Zhong Cheng, et al., "Somatosensory evoked potentials in patients with primary premature ejaculation" The Journal of Urology, vol. 158, No. 2, pp. 451-455, 1997.

Xin, Zhong Cheng, et al., "Penile Sensitivity in patients with primary premature ejaculation" The Journal of Urology, vol. 156, pp. 979-981, 1996.

Xin, Zhong Cheng, et al., "Efficacy of a Topical Agent SS-cream in the Treatment of Premature Ejaculation: Preliminary Clinical Studies" Yonsei Medical Journal, vol. 38, No. 2, pp. 91-95, 1997.

Yang, Claire C. et al., "Innervation of the Human Glans Penis" The Journal of Urology, vol. 161, pp. 97-102, 1999.

GP Kushla and JL Zatz, "Influence of pH on lidocaine penetration through human and hairless mouse skin in vitro", International Journal Pharmaceutics, 71 (1991) 167-173.

CA Lipinski; F Lombardo; BW Dominy and PJ Feeney, "Experimental and computational approaches to estimate solubility and permeability in drug discovery and development setting"; Advances in Drug Del Rev 46 (2001) 3-26.

HA McLure, AP Rubin, "Review of local anaesthetic agents", Minerva Anestesiology 71 (2005) 59-74.

Bridgette Israel et al.; "Transdermal Permeation of N-Acetyl-Glucosamine/NSAID Mutual Prodrugs", Pharmaceutical Development and Technology, Sep. 1-7, 2010, Early online (http://informahealthcare.com/eprint/2mqewiiPCyNpciMKfBAA/ful?tokenKey=).

Xudong Yuan and AC Capomacchia, "Physicochemical Studies of the Binary Eutectic of Ibuprofen and Ketoprofen for Enhanced Transdermal Drug Delivery", Drug Development and Industrial Pharmacy; 36, (10); 1168-1176; 2010.

Xudong Yuan and AC Capomacchia, "The Binary Eutectic of NSAIDs and Two Phase Liquid System for Enhanced Membrane Permeation"; Pharmaceutical Development and Technology, 1:1-10, 2005.

Valenta et al.; "The dermal delivery of lignocaine: influence of ion pairing" International Journal of Pharmaceutics 197 (2000) 77-85.

Chue, Pierre, "Gabapentin Treatment for Premature Ejaculation" The Canadian Journal of Psychiatry, vol. 49, No. 9, pp. 630-645, 2004.

Siek, T.j. et al., "Identification of Drugs and Other Toxic Compounds from Their Ultraviolet Spectra. Part III: Ultraviolet Absorption Properties of 22 Structural Groups." Journal of Forensic Sciences, vol. 21, No. 3, pp. 525-551, 1976.

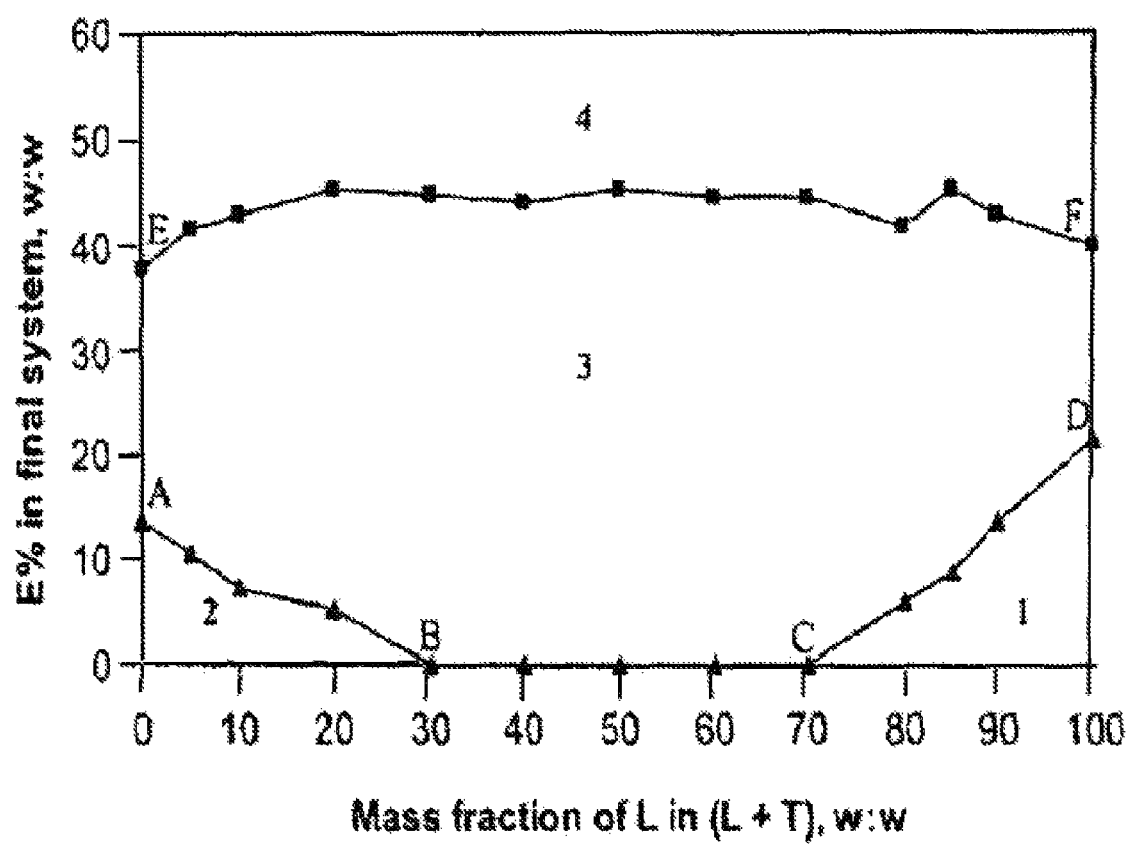

DESENSITIZING DRUG PRODUCT

CROSS-REFERENCE TO RELATED APPLICATIONS

This application is a continuation of U.S. patent application Ser. No. 13/145,743, filed Jul. 21, 2011, and entitled "DESENSITIZING DRUG PRODUCT," which is a National Phase Entry of PCT Application No. PCT/US2010/021705, filed Jan. 22, 2010, which claims the benefit of priority under 35 U.S.C §119(e) of U.S. Provisional Application No. 61/146,563 filed on Jan. 22, 2009, and entitled "DESENSITIZING DRUG PRODUCT," all of which are hereby incorporated herein by reference in their entirety and are to be considered a part of this specification.

FIELD OF THE INVENTION

The present invention relates to desensitizing drug products, methods of making desensitizing drug products and methods of using desensitizing drug products, including delivery of desensitizing drug products. According to an embodiment of the invention, the desensitizing drug product is a male genital desensitizer.

BACKGROUND OF THE INVENTION

Anesthetic products are known in the medical field and can be used for desensitization. EMLA® (lidocaine 2.5% and prilocaine 2.5%) cream has been used as a topical anesthetic. EMLA comprises lidocaine and prilocaine in an emulsified topical cream. Lidocaine is recognized as being safe and effective. It has been reported, however, that prilocaine use results in metabolites that are responsible for methemoglobinemia. Accordingly, alternatives to EMLA have been sought. See U.S. Pat. No. 6,299,902.

Desensitizing drug products have been used for treatment of males for premature ejaculation. That is, desensitizing drug products have been developed for application on the penis to help in temporarily slowing the onset of ejaculation, and can be referred to as male genital desensitizers or male genital desensitizer compositions. The U.S. Food and Drug Administration has published a monograph for over-the-counter products for the treatment of premature ejaculation.

SUMMARY OF THE INVENTION

The invention includes and provides compositions for the treatment of premature ejaculation. Such compositions include desensitizing drug products. The invention also includes and provides methods of making desensitizing drug products and methods of using desensitizing drug products, including delivery of desensitizing drug products.

The invention provides, among other things, metered spray bottles labeled for the treatment of premature ejaculation in males, wherein the metered spray bottles comprise male genital desensitizer compositions, wherein the male genital desensitizer compositions comprise an anesthetic agent; a first melting point depressing agent selected from the group consisting of thymol, methyl salicylate, phenyl salicylate, butylated hydroxytoluene, butylated hydroxyanisole, S(+)-ibuprofen, R(−)-ibuprofen, cineole, eugenol, capsaicin, eucalyptol, and an alcohol; and a second melting point depressing agent selected from the group consisting of thymol, methyl salicylate, phenyl salicylate, butylated hydroxytoluene, butylated hydroxyanisole, S(+)-ibuprofen, R(−)-ibuprofen, cineole, eugenol, capsaicin, eucalyptol, and an alcohol, and wherein the second melting point depressing agent is different from the first melting point depressing agent.

Methods for treating ejaculation in males also are provided according to the invention. The methods include the step of administering to a male subject a male genital desensitizer composition, wherein the male genital desensitizer compositions comprise an anesthetic agent; a first melting point depressing agent selected from the group consisting of thymol, methyl salicylate, phenyl salicylate, butylated hydroxytoluene, butylated hydroxyanisole, S(+)ibuprofen, R(−)-ibuprofen, cineole, eugenol, capsaicin, eucalyptol, and an alcohol; and a second melting point depressing agent selected from the group consisting of thymol, methyl salicylate, phenyl salicylate, butylated hydroxytoluene, butylated hydroxyanisole, S(+)-ibuprofen, R(−)ibuprofen, cineole, eugenol, capsaicin, eucalyptol, and an alcohol, and wherein the second melting point depressing agent is different from the first melting point depressing agent.

The administering can be performed using a metered spray. The administering can include 3 to 10 sprays (e.g., 3, 4, 5, 6, 7, 8, 9, or 10 sprays in one or a series of applications). Each spray can include about 10 mg lidocaine.

The anesthetic agent can be lidocaine. Preferably, prilocaine is not used or is not present. Preferably, menthol is not used or is not present. According to the invention, methemoglobinemia is to be avoided. In one embodiment, the anesthetic agent is lidocaine, the first melting point depressing agent is thymol, and the second melting point depressing agent is ethanol.

In various embodiments, the invention provides compositions and methods that are more effectively delivered to the user and thus safer than compositions and methods known in the art. For example, the invention includes the use of a eutectic compositions (e.g., comprising an anesthetic and a first melting point depressing agent, together with a second melting point depressing agent for forming an emulsion) that can (i) facilitate/enhance delivery of an anesthetic (e.g., lidocaine) through the stratum corneum, directly to nerves in the dermis. The composition, in accordance with an embodiment of the invention, more safely delivers the anesthetic to desensitize the nerves in the penis by creating a positive charge on the anesthetic, which reduces absorption into the bloodstream (e.g., systemic absorption). In some examples, the invention can allow for use of a smaller amount of anesthetic.

BRIEF DESCRIPTION OF THE DRAWINGS

FIG. 1 shows a partial phase diagram of lidocaine-thymol-ethanol in pH 9.2 carbonate buffer at 25° C.

DETAILED DESCRIPTION OF THE PREFERRED EMBODIMENT

The invention provides, among other things, desensitizing drug products that are useful for the treatment of premature ejaculation, among other things. The desensitizing drug product should possess transdermal absorption and efficacy. Preferably, the desensitizing drug product comprises at least one anesthetic agent (or solely one) and one or more melting point depressing agents. In a preferred embodiment, the desensitizing drug product contains only one anesthetic agent and two melting point depressing agents.

Anesthetic agents comprise those known in the art and modifications thereof. Such anesthetic agents include lidocaine, tetracaine, procaine, mepivacaine, bupivacaine, etidocaine. A preferred anesthetic agent is lidocaine, which should be a in a metered spray with approximately 10 milligrams per spray. Preferably, according to the invention, prilocaine is not present.

Melting point depressing agents also are known in the art, and include thymol, methyl salicylate, phenyl salicylate, butylated hydroxytoluene, butylated hydroxyanisole, S(+)-ibuprofen, R(−)-ibuprofen, cineole, eugenol, capsaicin, eucalyptol, and an alcohol, such as ethyl alcohol, isopropyl alcohol, propylene glycol, polyethylene glycol. Melting point suppressing agents can be used singly or any combination of the above. The presence of one or more melting point depressing agents is believed to allow for a degree of transdermal absorption of the anesthetic agent that is sufficient for the anesthetic agent to desensitize the treated area, such as the penis. Preferably, two different melting point depressing agents are employed.

The terms "about" and "approximately" in the context of numerical values and ranges refers to values or ranges that approximate or are close to the recited values or ranges such that the invention can perform as intended, such as having a desired rate, amount, degree or extent of absorption and desensitization, as is apparent from the teachings contained herein. Thus, this term encompasses values beyond those simply resulting from systematic error. By "substantially," as recognized by the skilled person, it is meant in this and similar contexts that the products and methods are suitable for their intended purpose.

All ranges set forth herein in the summary and description of the invention and the claims include all numbers or values thereabout or therebetween of the numbers of the range. The ranges of the invention expressly denominate and set forth all integers, decimals and fractional values in the range The term "treating" in its various grammatical forms in relation to the present invention refers to, depending on context, avoiding, preventing, curing, reversing, attenuating, alleviating, minimizing, suppressing or halting the deleterious effects of a disease state, disease progression, disease causative agent or other abnormal or undesired condition, as recognized by the skilled person or a person in need of treatment. In a preferred embodiment of the invention, premature ejaculation is treated.

EXAMPLES

The invention is further described by the following examples, which are illustrative of the many aspects of the invention, but do not limit the invention in any manner.

Example 1

Formation and advantages of a eutectic solution comprising lidocaine, thymol, and ethanol:

Lidocaine is a crystalline material in its natural state and, as such, does not penetrate the skin or provide analgesic activity unless prepared and applied in a solution. Physicians typically inject lidocaine HCl solution subcutaneously to deliver an analgesic effect, or topically apply a cream containing lidocaine free base (e.g., EMLA). In contrast to these methods, the invention includes a topically effective lidocaine eutectic solution, and methods for making and using the same. Such a solution can be prepared by mixing lidocaine free base with thymol to form a eutectic (e.g., an oleaginous mass in which the lidocaine free base is dissolved). Then ethanol is added as a second melting point depresser. Then, an aqueous formulation with a predetermined acidity can be added to the lidocaine-thymol solution, such that lidocaine free base is in dynamic equilibrium with singly charged lidocaine. The resulting invention can achieve advantages through the combination of:

1. Penetrating the Stratum Corneum;
2. Delivering a localized analgesic effect on nerves in the dermis; and
3. Slowing systemic absorption of the lidocaine.

Step 1: Forming a Eutectic Solution

By mixing two agents (e.g., lidocaine free base and thymol), a eutectic can be created, which is an oily mass that presents with a lower melting temperature than either of the two ingredients separately. The lower melting temperature of the eutectic can contribute to increased skin permeation and solubilization of the lidocaine free base, which has a low solubility in water but is very soluble in lipophilic or oily materials. Ethanol, a transdermal permeation enhancer, can be added to further enhance penetration through the stratum corneum. The resulting composition can allow, for example, up to 10% lidocaine free base to be prepared in solution.

Step 2: Positively Charged Lidocaine Cation

After the ethanol eutectic solution is prepared, it can be mixed with an aqueous solution containing suitable surfactants (e.g., TWEEN and/or SPAN, available from Atlas Chemical Company, poloxamers, carbomers, glyceryl fatty acid esters, and similar agents known to act as surfactants to aid emulsification) and other ingredients (e.g., any pharmaceutical oil like esters of long chain fatty acids such as isopropyl myristate, or isopropyl palmitate or other pharmaceutically accepted solvent (such as but not limited to mineral oil, glycerin, propylene glycol, polyethelene glycol) used to solubilize an active lipophilic ingredient like lidocaine free base prior to mixing (Waring blender, homogenizer, shaking in bottle, or some like device for mixing, etc.) with a suitable surfactant and a second immiscible liquid like water or an aqueous solution to form an emulsion), such that an oil-in-water emulsion is formed (e.g., an oil-in-water emulsion with the oil constituting the internal phase (the oil is formed from mixing vigorously lidocaine (8.33%) and thymol (1.0%) which is 9.33% of the total weight of the product. Emulsions can become unstable if the internal phase exceeds 70-75% of the total ingredients, so a range for the oil phase can be 3.0%-70.0%, knowing that [% oil phase+% water phase=100%]; the surfactant can be in the range of 0.3-15%). The aqueous solution can be prepared at an acidity where lidocaine free base exists in dynamic equilibrium with the singly protonated cationic form of lidocaine (e.g., The pKa of lidocaine is circa 7.9 and at pH 7.9 it is 50% ionized such that it exists as 50% free base and 50% singly protonated cation. A suitable pH range to assure at least 10% ionization is: pH 6.9-8.9, where at pH 8.9 it will be 10% ionized and at pH 6.9 it will be 90% ionized). One purpose of creating a positively charged lidocaine cation is that the charge can prevent skin absorption and, therefore, the cation in emulsion can act as a reservoir for lidocaine free base. This effect can slow skin permeation of lidocaine free base and its systemic absorption rate, thereby prolonging its local anesthetic action.

SUMMARY

These two steps can help achieve three goals. First, the composition including the eutectic solution combining thymol and lidocaine free base coupled with ethanol can create an enhanced transdermal delivery system that penetrates the stratum corneum. Second, the effect of the positively charged lidocaine cation can help produce a local analgesic effect in the dermis where the nerves are located. Third, the effect of the positively charged lidocaine cations can also slow systemic absorption. Thus, embodiments of the invention can solve the problems associated with topical lidocaine absorption and can allow the invention (e.g., including PROMESCENT™, available from G&H Brands LLC) to deliver prolonged, topical anesthetic activity where desired.

Example 2

Active and inactive ingredients of a desensitizing drug product according to the invention:
Lidocaine: 8.33%, w/w (weight/weight)
Thymol: 1.0%, w/w
Ethanol: 10%, w/w
Base: 80.7%, w/w
For 1000 grams (1 kg) of product:
Weigh out the following amounts of ingredients:
83 grams Lidocaine, USP
10 grams Thymol, USP
100 grams Ethanol, USP
807 grams formulation base Optionally, a fragrance can be included. An example of such a product would be:
Lidocaine: 8.33%, w/w (weight/weight)
Thymol: 1.0%, w/w
Ethanol: 10%, w/w
Base: 78.2%, w/w Range (77.7-80.6%)
Fragrance 2.5% Range (0.1-3%)

Weights are approximate. The products are formulated for administration as a metered spray.

Example 3

To make a drug product according to Example 1 (can be adjusted for optional fragrance):
1. Add the 10 grams of thymol and 83 grams of lidocaine; triturate (grind in mortar and pestle or some other device) until an oily paste is formed.
2. To the oily paste, add the ethanol all at once with mixing until a clear solution is formed.
3. To the clear solution, add the formulation base (such as Cetaphil and its equivalents from Galderma or Walgreens) all at once and place on a mixing device and mix to desired consistency.

It should be noted that the formulation base contains the following: water ACRYLATE CROSSPOLYMER, BENZYL ALCOHOL, CETEARETH 20, CETEARYL ALCOHOL, CITRIC ACID, DIMETHICONE, FARNESOL, GLYCERIN, HYDROGENATED POLYISOBUTENE, MACADAMIA TERNIFOLIA SEED OIL, PANTHENOL, PHENOXYETHANOL, PURIFIED WATER (AQUA), SODIUM HYDROXIDE, STEAROXYTRIMETHYLSILANE STEARYL ALCOHOL, TOCOPHERYL ACETATE (VITAMIN E). An alternative formulation base can contain the following: water, cetyl alcohol, propylene glycol, sodium lauryl sulfate, stearyl alcohol; preserved with methylparaben, propylparaben, butylparaben. Variations and alternatives can be readily prepared by one of ordinary skill in the art.

To prepare the final product, use a Cito-Unguator 2000 set on the emulsion setting. This setting allows for 8 minutes mixing time. Other mixers with appropriate settings and speed also can be used.

Over mixing by using the emulsion+ setting of the Cito-Unguator 2000 (more than about 30 minutes) causes the emulsion to foam excessively and separate into two phases—foam and solution—and cannot be remixed. Thus, mixing times as well as RPM appear to be important parameters in the mixing/emulsification process. Even if not most optimum, the product formed according to the above method does not break for a period of at least over the three weeks while at room temperature.

Other appropriate formulations that can be adapted for use according to the invention are disclosed in U.S. Pat. No. 6,299,902, and such formulations are hereby incorporated by reference. For example, an appropriate formulation can be adapted from Example 1 of U.S. Pat. No. 6,299,902, as follows:

A. Melting Point Depression of Lidocaine (L) by Thymol (T)

The melting points of lidocaine and thymol are 68° C. and 52° C., respectively. After preparing and storing the mixtures consisting of lidocaine and thymol in the L:T ratios from 1:9 to 9:1 (w:w) at 25° C., the melting states of the mixtures were examined weekly for 3 months using an optical microscope. Although the mixtures within L:T ratios of 3:7 to 7:3 (w:w) spontaneously form a homogeneous oil at ambient temperature, some crystals and oil co-exist in the mixtures outside this range. For example, in the mixture with the L:T ratio of 8:2 (w:w), a large portion of lidocaine remains as crystalline solid at 25° C.

Lidocaine and thymol were chemically stable in the mixtures that formed a homogenous oil. Compositional analysis of the mixture containing 50% lidocaine and 50% thymol (w:w) that was stored at 25° C. for 6 months, utilizing gas chromatography-mass spectrometry (GC-MS), showed essentially complete recovery of both lidocaine (101.6+−3.98%) and thymol (99.36+−2.22%) (n=3).

B. Melting Point Depression of Lidocaine (L) by Ethyl Alcohol (E) in Aqueous Dispersions Lidocaine was dispersed into a solution containing ethyl alcohol and water, and oil droplets formed at 25° C., which is below the melting point of lidocaine. To measure the effect of ethyl alcohol on the melting point depression of lidocaine in the aqueous dispersion, lidocaine (0.5 g) was mixed (at 25° C.) with 1.0 g, 1.5 g, 2.0 g, and 2.5 g of ethyl alcohol, and then a pH 9.2 phosphate buffer was added up to 10 g. Replicate samples of these mixtures were prepared at room temperature then stored at 25° C., 15° C., and 4° C. During storage, the melt states of the samples were examined weekly for 3 months using an optical microscope. Table 2 shows that when the ethyl alcohol contents were 20% or less, lidocaine did not completely melt at 25° C. When the ethyl alcohol contents were 25% (or higher, not shown in the table); the lidocaine crystals undergo a solid to liquid phase change into an oil even at 15° C. Clearly, the melting point of lidocaine in these dispersions is inversely dependent on the ethyl alcohol content; that is, the higher the ethyl alcohol content, the lower the melting point of lidocaine.

After ultracentrifugation, a portion of the oil phase was removed from the mixture containing 25% ethyl alcohol using a 25 μL microsampling tube, and the weight was measured using a tared weighing. The oil was then dissolved in methylene chloride and analyzed by GC-MS. The results show that the concentration of lidocaine was 73% (w:w) in the oil, indicating that the oil was a mixture of lidocaine, ethyl alcohol, and possibly some water.

TABLE 2

Melt States of Dispersions containing Lidocaine[a],
Ethyl Alcohol (E), and Water at Different Temperatures

| °C.\E %[b] | 10 | 15 | 20 | 25 |
|---|---|---|---|---|
| 25 | S | S | S | O |
| 15 | S | S | S | O |
| 4 | S | S | S | S |

[a]5% of total composition by weight
[b]% of total composition by weight
S - solid crystals present
O - oil without crystals C. Melting Point Depression of Lidocaine (L) by Thymol (T) and Ethyl Alcohol (E) in Aqueous Dispersions Since thymol and ethyl alcohol can individually depress the melting point of lidocaine, the effect of the two compounds in combination on the melting point of lidocaine was studied.

A 3-factor factorial design as shown in Table 3 was used to examine the melting states of lidocaine in the presence of both thymol and ethyl alcohol simultaneously at different temperatures. Since thymol alone is capable of depressing the melting point of lidocaine at and below 25° C. within the L:T ratios of 3:7-7:3 (w:w). only the higher L:T ratios higher than this range were included in the study.

TABLE 3

Melt States of Dispersions containing Lidocaine (L), Thymol (T),
Ethyl Alcohol (E), and Water at Different Temperatures

| LT[a] | °C. | 10% E[a] | 15% E | 20% E | 25% E |
|---|---|---|---|---|---|
| 90:10 | 25 | S | O[III] | O[IV] | O |
|  | 15 | S | S | S | O |
|  | 4 | S | S | S | O |
| 85:15 | 25 | O[I] | O[II] | O[V] | O |
|  | 15 | O | O | O | O |
|  | 4 | S | S | S | O |
| 80:20 | 25 | O | O | O | O |
|  | 15 | O | O | O | O |
|  | 4 | S | O | O | O |

S = solid crystal present
O = oil without crystals
[a]L:T and % E by weight

Lidocaine (0.5 g) was mixed (at ambient temperature) with 0.125 g, 0.088 g, and 0.056 g of thymol and 1.0 g, 1.5 g, 2.0 g, and 2.5 g of ethyl alcohol, then a pH 9.2 phosphate buffer was added up to 10 g. Replicate samples of these mixtures were prepared at 25° C. and were stored at 25° C., 15° C., and 4° C. for three months. During storage, the melt states of the mixtures were examined weekly for three months using an optical microscope. The results in Table 3 show that there is a clear relationship among the L:T ratios, ethyl alcohol content, and melt states of lidocaine in the mixture. The lower the L:T ratios and the higher the ethyl alcohol content, the lower the melting point range of the solid components in the mixture as shown by the attainment of the melt state. Comparing these results, as well as the effect of thymol alone on the melting point of lidocaine with the data in Table 2, it is clear that a more pronounced melting point depression effect was demonstrated when thymol and ethyl alcohol were used simultaneously rather than individually. Thus, the use of thymol and ethyl alcohol in combination allows the preparation of the two-phase melt systems with highest possible L:T ratio and lowest ethyl alcohol content at 25° C.

D. Distribution of Lidocaine (L) and Thymol (T) Between the Aqueous and Oil Phases in the Melt Systems As shown in Table 3, Melt Systems I, II, III, IV, and V consisted of the homogeneous oil and the aqueous phase without crystals present at 25° C. Compared with other melt systems listed in the table, these systems contained relatively lower concentrations of thymol and ethyl alcohol and accordingly were selected for further study, since minimizing the concentrations of thymol and ethyl alcohol in the compositions while still retaining high concentrations of lidocaine in the oil phase is preferred. After separating the oil droplets from the aqueous phase by ultra-centrifugation at 20,000 rpm for 30 minutes at 25° C., the oil phases from Melt Systems II, III, IV, and V were analyzed by GC-MS, as described above, to determine both lidocaine and thymol concentrations. The aqueous phase from Melt System III was also analyzed after the extraction with methylene chloride. The chemical compositions of the oil phase in these melt systems are shown in Table 4.

TABLE 4

Composition of Oil Phase in Selected Two-Phase Melt Systems

| Melt Systems | % L[b] | % T[b] | % Residual[c] |
|---|---|---|---|
| II[a] | 80.1 | 15.1 | 4.8 |
| III[a] | 87.0 | 10.6 | 2.4 |
| IV[a] | 85.9 | 11.2 | 2.9 |
| V[a] | 81.2 | 16.2 | 2.6 |

[a]Source: Table 3
[b]% L or % T = amount (g) of lidocaine or thymol detected per 100 g of the oil phase
[c]Residual = 100 − (% L + % T)

The concentrations of lidocaine in the oil phases of the melt systems analyzed were consistently higher than 80% (w:w) and reached as high as 87% (w:w) as evidenced by Melt System III. The sum of lidocaine and thymol in the oil phase was less than 100%, due to the presence of ethyl alcohol and possibly a trace amount of water. This also indicates that in the two-phase melt systems, nearly all of the ethyl alcohol is present in the aqueous phase. It can also be seen that the higher the initial L:T ratio, the higher the lidocaine concentration in the oil phase.

As shown in Table 5, the GC-MS data indicate that the concentrations of lidocaine and thymol in the aqueous phase of Melt System III were 1.09% and 0.09% (w:w), respectively. Based on the initial composition of the melt system and the concentrations of lidocaine and thymol in both the aqueous and oil phases, the quantities of lidocaine and thymol in both the aqueous phase and the oil phase were estimated. The results in Table 5 show that approximately 80% by weight of the total lidocaine and approximately 85% by weight of the total thymol are present in the oil phase, while the remaining amounts are present in the aqueous phase.

TABLE 5

Distribution of Lidocaine (L) and Thymol (T) Between Oil Phase and Aqueous Phase (aq) of Melt System III[a]

| | Conc in oil[b] % | Percentage in oil[c] % | Conc in aq[b] % | Percentage in aq[c] % |
|---|---|---|---|---|
| L | 87.00 | 79.20 | 1.09 | 20.80 |
| T | 10.60 | 85.13 | 0.09 | 14.88 |

[a]Source: Table 3
[b]Concentration in oil phase or aqueous phase = amount (g) detected per 100 g of oil phase or aqueous phase
[c]Percentage in oil phase or aqueous phase = amount (g) in oil phase or aqueous phase/total amount (g) in the whole system × 100

It can thus be seen that generation of a homogenous oil phase, as in the two phase melt systems shown in Table 3, depends on the relative amounts of the local anesthetic, LA, the first melting point depressing agent, MP-A, and the second melting point depressing agent, MP-B, in the systems. When thymol (as the MP-A) and/or ethyl alcohol (as the MP-B) are present in insufficient amounts, a two phase melt system is not achieved at ambient temperature, and instead crystals remain in the composition. A preferred two phase melt system is generally characterized by high lidocaine: thymol ratio and a relatively low amount of ethyl alcohol.

Example 5

Administration, Directions and Labeling:

The desensitizing drug product according to the invention can help in the treatment of premature ejaculation. It can be used for temporary male genital desensitization, helping to slow the onset of ejaculation, prolonging the time until ejaculation or retarding the onset of ejaculation. It can be used for reducing oversensitivity in the male in advance of intercourse.

The product is to be applied to the penis to help in the temporary slowing of the onset of ejaculation. With a lidocaine metered spray, apply 3 or more sprays, not to exceed 10, to head and shaft of penis before intercourse, or use as directed by a doctor or physician. Wash product off after intercourse. Administration by metered spray is known to the person skilled in the art. Metered spray bottles (flasks, etc.) are known in the art and commercially available.

In general, the metered spray bottle can include essentially any spray bottle approved by the FDA for dispensing lidocaine, such as the metered spray bottles manufactured by Packaging Concepts Assoc., LLC (4925 Park Ridge Blvd. Boynton Beach, Fla. 33426). In one example, the metered spray bottle can be a 1.0 or 2.0 FL. OZ. CR MPAK Child Resistant Spray Dispenser, or equivalent thereof, available from Packaging Concepts Assoc., LLC. The metered spray bottle can be child-resistant. The metered spray bottle can be a non-aerosol dispenser. In one example, the metered spray bottle can be adapted such that about 130 microliters of composition, containing about 10 mg of lidocaine, is dispensed in each spray.

Contact with the eyes should be avoided. If the user or partner develops a rash or irritation, such as burning or itching, use of the product should be discontinued. If symptoms persist, consult a doctor of physician.

Premature ejaculation may be due to a condition requiring medical supervision. If a product according to the invention does not provide relief, use should be discontinued and a doctor or physician should be consulted.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

Example 6

FIG. 1 shows a partial phase diagram of lidocaine-thymol-ethanol in pH 9.2 carbonate buffer at 25° C. The total amount of L+T in the system was 4.76% prior to titration with ethanol. The border lines ABCD and EF divide the diagram into four regions" (1) solid lidocaine remaining, (2) solid thymol remaining, (3) two-phase (oil and aqueous) system, and (4) monophase solution. In various embodiments, a eutectic composition according to the invention (e.g., an oily mass formed upon mixing compounds like local anesthetics like lidocaine or benzocaine in their crystalline state with a terpene like thymol or cineole, also in their crystalline state) can be formed according to FIG. 1. The oily mass exists at a temperature lower than that of either crystalline agent allowing greater concentrations of either agent to be solubilized compared to using a pharmaceutical oil like isopropyl myristate. In the case of lidocaine, it is readily soluble in the oil formed from the eutectic and may be easily emulsified for topical delivery. In preferred embodiments, the inventive composition are formulated to fall just in the area describing the two phase melt (region 3). Eutectics can enhance drug permeation because their formation results in a lower melting temperature which is associated with greater drug permeation. Ethanol can function as a permeation enhancer.

Example 7

The eutectic formulation utilizing the two step melting point depression process was administered to 5 healthy male volunteers to determine the systemic (e.g., serum) levels of lidocaine 1 and 4 hours after administration. The maximum dose allowed for the treatment of premature ejaculation (10 sprays, 10 mg lidocaine per spray) was administered by a metered dose spray and serum lidocaine levels were determined 1 and 4 hours later. In 4 of the 5 volunteers, serum lidocaine levels were undetectable at both 1 and 4 hours. In the fifth volunteer, serum lidocaine levels of 0.4 micrograms per milliliter were found at both time intervals. This level (0.4 micrograms/ml) is one third the lower limit of the therapeutic range (e.g., the amount of lidocaine that is acceptable in the blood) and one fifteenth of the lower limit of the toxic range. The analysis was preformed by gas chromatography by an independent laboratory (Central Medical laboratory, 10554 Progress Way, Cypress, Calif. 90630). These blood results show that this inventive method of treating premature ejaculation is associated with minimal to no risk of side effects related to systemic lidocaine toxicity.

What is claimed is:

1. A method of treating premature ejaculation in a patient, the method comprising:
    administering to a surface of a penis a pharmaceutical composition comprising lidocaine, thymol, 10% by weight ethanol based on the total weight of the pharmaceutical composition, and a base, the pharmaceutical composition having a ratio of lidocaine to thymol of about 9:1 by weight, and wherein the pharmaceutical composition does not contain prilocaine; and
    relieving symptoms of premature ejaculation.
2. The method of claim 1, wherein the base comprises an aqueous solution, and wherein the aqueous solution comprises a pH in the range of about 6.9 to about 8.9.

3. The method of claim 2, wherein the aqueous solution comprises a pH of about 6.9.

4. The method of claim 2, wherein the aqueous solution comprises a pH of about 7.9.

5. The method of claim 2, wherein the aqueous solution comprises a pH of about 8.9.

6. The method of claim 1, wherein the administering is performed using a metered spray.

7. The method of claim 6, wherein the administering comprises a number of sprays in the range of 3 sprays to 10 sprays.

* * * * *